United States Patent
Nappa et al.

(10) Patent No.: US 10,995,047 B2
(45) Date of Patent: May 4, 2021

(54) PROCESS FOR THE REDUCTION OF RfC=CX IMPURITIES IN FLUOROOLEFINS

(71) Applicant: THE CHEMOURS COMPANY FC, LLC, Wilmington, DE (US)

(72) Inventors: Mario Joseph Nappa, Leesburg, FL (US); Xuehui Sun, Swedesboro, NJ (US); David Richard Corbin, West Chester, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 16/446,840

(22) Filed: Jun. 20, 2019

(65) Prior Publication Data

US 2019/0300461 A1 Oct. 3, 2019

Related U.S. Application Data

(63) Continuation of application No. 15/973,598, filed on May 8, 2018, now Pat. No. 10,343,961, which is a continuation of application No. 15/609,292, filed on May 31, 2017, now Pat. No. 10,246,388, which is a continuation of application No. 14/932,042, filed on Nov. 4, 2015, now abandoned, which is a continuation of application No. 14/210,640, filed on Mar. 14, 2014, now abandoned.

(60) Provisional application No. 61/791,304, filed on Mar. 15, 2013.

(51) Int. Cl.
C07C 17/389 (2006.01)
C07C 17/25 (2006.01)
C07C 17/087 (2006.01)

(52) U.S. Cl.
CPC .......... *C07C 17/389* (2013.01); *C07C 17/087* (2013.01); *C07C 17/25* (2013.01); *Y02P 20/582* (2015.11)

(58) Field of Classification Search
CPC ....... C07C 17/389; C07C 21/18; C07C 17/25; C07C 17/383; C07C 17/206; C07C 17/087
See application file for complete search history.

(56) References Cited

U.S. PATENT DOCUMENTS

| | | |
|---|---|---|
| 4,906,796 A | 3/1990 | Yates |
| 5,087,778 A | 2/1992 | Yates |
| 5,233,107 A | 8/1993 | Jansen |
| 5,347,822 A | 9/1994 | Lavin et al. |
| 5,425,242 A | 6/1995 | Dunne et al. |
| 5,600,040 A | 2/1997 | Corbin et al. |
| 5,710,352 A | 1/1998 | Tung |
| 5,895,825 A | 4/1999 | Elsheikh et al. |
| 6,124,510 A | 9/2000 | Elsheikh et al. |
| 6,472,573 B1 | 10/2002 | Yamamoto et al. |
| 7,084,312 B1 | 8/2006 | Huber et al. |
| 7,084,315 B2 | 8/2006 | Corr et al. |
| 7,084,316 B2 | 8/2006 | Ohno et al. |
| 7,384,519 B2 | 6/2008 | Cottrell et al. |
| 7,485,760 B2 | 1/2009 | Wang et al. |
| 7,563,936 B2 | 7/2009 | Wang et al. |
| 7,597,744 B2 | 10/2009 | Thomas et al. |
| 8,247,624 B2 | 8/2012 | Merkel et al. |
| 8,259,264 B2 | 8/2012 | Devic et al. |
| 8,288,598 B2 | 10/2012 | Wang et al. |
| 8,337,595 B2 | 12/2012 | Thomas et al. |
| 2007/0135617 A1 | 6/2007 | Ohno |
| 2007/0197843 A1 | 8/2007 | Ohno |
| 2009/0240090 A1 | 9/2009 | Merkel et al. |
| 2011/0105809 A1 | 5/2011 | Devic et al. |
| 2011/0172470 A1 | 7/2011 | Hamasaki et al. |
| 2012/0065437 A1 | 3/2012 | Merkel et al. |
| 2012/0203037 A1 | 8/2012 | Sharratt et al. |
| 2012/0266750 A1 | 10/2012 | Thomas et al. |

FOREIGN PATENT DOCUMENTS

| | | |
|---|---|---|
| CN | 102076645 A | 5/2011 |
| GB | 2492847 A | 1/2013 |
| JP | 64-40436 A | 2/1989 |
| JP | 2013-508265 A | 3/2013 |
| WO | 2011/045559 A1 | 4/2011 |

*Primary Examiner* — Jafar F Parsa

(74) *Attorney, Agent, or Firm* — McNees Wallace & Nurick LLC

(57) ABSTRACT

This disclosure relates to processes which involve: contacting a mixture comprising at least one fluoroolefin and at least one impurity with at least one zeolite to reduce the concentration of the at least one impurity in the mixture; and the at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that the at least one zeolite is not zeolite 4A. This disclosure also relates to processes for making at least one hydrotetrafluoropropene product selected from the group consisting of $CF_3CF{=}CH_2$, $CF_3CH{=}CHF$, and mixtures thereof; and relates to processes for making at least one hydrochlorotrifluoropropene product selected from the group consisting of $CF_3CCl{=}CH_2$, $CF_3CH{=}CHCl$, and mixtures thereof.

30 Claims, No Drawings

PROCESS FOR THE REDUCTION OF $R_fC≡CX$ IMPURITIES IN FLUOROOLEFINS

CROSS REFERENCE TO RELATED APPLICATIONS

The present application is a continuation application of U.S. patent application Ser. No. 15/973,598 filed May 8, 2018, which is continuation application of U.S. patent application Ser. No. 15/609,292 filed May 31, 2017, now U.S. Pat. No. 10,246,388, which is a continuation application of U.S. patent application Ser. No. 14/932,042 filed Nov. 4, 2015, which is a continuation application of U.S. patent application Ser. No. 14/210,640 filed Mar. 14, 2014, which claims benefit of provisional U.S. Provisional Patent Application No. 61/791,304 filed Mar. 15, 2013, the entire contents of which are incorporated herein by reference.

BACKGROUND OF THE INVENTION

The present disclosure relates to a process for reducing the concentration of $R_fC≡CX$ impurities in fluoroolefins by contact with a zeolite.

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for chemical compounds that have both low ozone depleting potentials (ODPs) and low global warming potentials (GWPs).

SUMMARY OF THE INVENTION

The present disclosure provides a process comprising: contacting a mixture comprising at least one fluoroolefin and at least one $R_fC≡CX$ impurity with at least one zeolite to reduce the concentration of said at least one $R_fC≡CX$ impurity in said mixture; wherein: (a) $R_f$ is a straight-chain perfluorinated alkyl group, and X is H, F, Cl, Br or I; and (b) said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A. The present disclosure also provides a process comprising: contacting a mixture comprising at least one fluoroolefin and at least one $R_fC≡CX$ impurity with at least one zeolite to reduce the concentration of said at least one $R_fC≡CX$ impurity in said mixture; wherein: (a) $R_f$ is a straight-chain perfluorinated alkyl group, and X is H, F, Cl, Br or I; and (b) said at least one zeolite comprises a zeolite having pore opening of at least about 5 Angstroms and Sanderson electronegativity of no more than about 2.6, and mixtures thereof.

The present disclosure also provides a process for making at least one hydrotetrafluoropropene product selected from the group consisting of $CF_3CF=CH_2$, $CF_3CH=CHF$, and mixtures thereof. The process comprises: (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CF_2H$, $CF_3CF_2CH_3$, and mixtures thereof to produce a product mixture comprising $CF_3C≡CH$ impurity and said at least one hydrotetrafluoropropene product; (b) contacting said product mixture with at least one zeolite to reduce the concentration of said $CF_3C≡CH$ impurity in said product mixture; and (c) recovering said at least one hydrotetrafluoropropene product having reduced concentration of said $CF_3C≡CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof provided that said at least one zeolite is not zeolite 4A. The present disclosure also provides a process for making at least one hydrotetrafluoropropene product of the formula $CF_3CF=CH_2$. The process comprises: (a) dehydrohalogenating at least one starting material selected from the group consisting of $CF_3CFClCH_3$, $CF_3CHFCH_2F$, $CF_3CF_2CH_3$, and mixtures thereof to produce a product mixture comprising $CF_3C≡CH$ impurity and said at least one hydrotetrafluoropropene product; (b) contacting said product mixture with at least one zeolite to reduce the concentration of said $CF_3C≡CH$ impurity in said product mixture; and (c) recovering said at least one hydrotetrafluoropropene product having reduced concentration of said $CF_3C≡CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A. The present disclosure also provides a process for making at least one hydrotetrafluoropropene product selected from the group consisting of $CF_3CF=CH_2$, $CF_3CH=CHF$, and mixtures thereof. The process comprises: (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CF_2H$, $CF_3CF_2CH_3$, and mixtures thereof to produce a product mixture comprising $CF_3C≡CH$ impurity and said at least one hydrotetrafluoropropene product; (b) contacting said product mixture with at least one zeolite to reduce the concentration of said $CF_3C≡CH$ impurity in said product mixture; and (c) recovering said at least one hydrotetrafluoropropene product having reduced concentration of said $CF_3C≡CH$ impurity; wherein said at least one zeolite comprises a zeolite having pore opening of at least about 5 Angstroms and Sanderson electronegativity of no more than about 2.6, or combination thereof.

The present disclosure also provides a process for making at least one hydrochlorotrifluoropropene product selected from the group consisting of $CF_3CCl=CH_2$, $CF_3CH=CHCl$, and mixtures thereof. The process comprises: (a) dehydrohalogenating at least one starting material selected from the group consisting of $CF_3CCl_2CH_3$, $CF_3CHClCH_2Cl$, $CF_3CHClCH_2F$, $CF_3CH_2CHCl_2$, $CF_3CHFCH_2Cl$, $CF_3CFClCH_3$, $CF_3CH_2CHFCl$, and mixtures thereof to produce a product mixture comprising $CF_3C\equiv CH$ impurity and said at least one hydrochlorotrifluoropropene product; (b) contacting said product mixture with at least one zeolite to reduce the concentration of said $CF_3C\equiv CH$ impurity in said product mixture; and (c) recovering said at least one hydrochlorotrifluoropropene product having reduced concentration of said $CF_3C\equiv CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A.

DETAILED DESCRIPTION OF THE INVENTION

Fluoroolefins have been found to have low ODPs and low GWPs and have been regarded as potential replacements for HFCs in many applications. For example, $CF_3 12 CF=CH_2$ (HFO-1234yf) and $CF_3CH=CHF$ (HFO-1234ze), having zero ODPs and low GWPs, have been identified as potential refrigerants. For another example, $CF_3CH=CHCl$ (HCFO-1233zd) and $CF_3CCl=CH_2$ (HCFO-1233xf), having low ODPs and low GWPs, may be used as foam expansion agents. HCFO-1233zd is also an intermediate in the production of HFO-1234ze, and HCFO-1233xf is an intermediate in the production of HFO-1234yf.

It has been found that $R_fC\equiv CX$ impurities, such as $CF_3C\equiv CH$, are often present in the fluoroolefin products. Since $R_fC\equiv CX$ impurities might be highly toxic, they need to be removed from the fluoroolefin products.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B is true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

HFO-1234ze may exist as one of two configurational isomers, E or Z. HFO-1234ze as used herein refers to the isomers, E-HFO-1234ze or Z-HFO-1234ze, as well as any combinations or mixtures of such isomers.

HCFO-1233zd also may exist as one of two configurational isomers, E or Z. HCFO-1233zd as used herein refers to the isomers, E-HCFO-1233zd or Z-HCFO-1233zd, as well as any combinations or mixtures of such isomers.

$CF_3CF=CHCl$ (HCFO-1224yd) also may exist as one of two configurational isomers, E or Z. HCFO-1224yd as used herein refers to the isomers, E-HCFO-1224yd or Z-HCFO-1224yd, as well as any combinations or mixtures of such isomers.

$CF_3CCl=CHCl$ (HCFO-1223xd) also may exist as one of two configurational isomers, E or Z. HCFO-1223xd as used herein refers to the isomers, E-HCFO-1223xd or Z-HCFO-1223xd, as well as any combinations or mixtures of such isomers.

The term "pore opening", as used herein, means the mouth of the pore by which the $R_fC\equiv CX$ impurity enters the body of the pore.

The term "$R_fC\equiv CX$ impurity", as used herein, means the impurity of the formula $R_fC\equiv CX$ present in a fluoroolefin product.

The term "fluoroolefin", as used herein, means a molecule containing hydrogen, carbon, fluorine, and a carbon-carbon double bond and optionally chlorine. Examples are described throughout the instant specification.

The term "hydrofluoroolefin", as used herein, means a molecule containing hydrogen, carbon, fluorine, and a carbon-carbon double bond.

The term "hydrochlorofluoroolefin", as used herein, means a molecule containing hydrogen, carbon, chlorine, fluorine, and a carbon-carbon double bond.

The term "alkyl", as used herein, either alone or in compound words such as "perfluorinated alkyl group", includes cyclic or acyclic and straight-chain or branched alkyl groups having 1-6 carbon atoms, such as, methyl, ethyl, n-propyl, i-propyl, n-butyl, sec-butyl, tert-butyl, isobutyl, n-pentyl, isopentyl, neopentyl, 3-methylbutane, 2,3-dimethyl-propane, n-hexyl, and the various other isomers of n-hexyl.

The term "straight-chain perfluorinated alkyl group", as used herein, means a straight-chain alkyl group wherein all hydrogens on carbon atoms have been substituted by fluorines. Examples of a straight-chain perfluorinated alkyl group include $-CF_3$, $-CF_2CF_3$ and $-CF_2CF_2CF_3$.

The term "aralkyl", as used herein, means an alkyl group wherein one or more hydrogens on carbon atoms have been substituted by an aryl group, such as phenyl or naphthyl and the like. Examples of an aralkyl group include $C_6H_5CH_2-$, phenethyl, and the like.

The term "ppm", as used herein, means parts per million by weight.

The term "dehydrohalogenation", as used herein, means dehydrofluorination or dehydrochlorination. The term "dehydrohalogenating", as used herein, means dehydrofluorinating or dehydrochlorinating. The term "dehydrohalogenated", as used herein, means dehydrofluorinated or dehydrochlorinated.

The term "dehydrofluorination", "dehydrofluorinating" or "dehydrofluorinated", as used herein, means a process during which hydrogen and fluorine on adjacent carbons in a molecule are removed.

The term "dehydrochlorination", "dehydrochlorinating", or "dehydrochlorinated", as used herein, means a process during which hydrogen and chlorine on adjacent carbons in a molecule are removed.

The term "an elevated temperature", as used herein, means a temperature higher than the room temperature.

The present disclosure provides a process for reducing the amount of $R_fC \equiv CX$ impurity from fluoroolefin by contacting fluoroolefin containing $R_fC \equiv CX$ impurity with a zeolite. The process comprises: contacting a mixture comprising at least one fluoroolefin and at least one $R_fC \equiv CX$ impurity with at least one zeolite to reduce the concentration of said at least one $R_fC \equiv CX$ impurity in said mixture; wherein: (a) $R_f$ is a straight-chain perfluorinated alkyl group, and X is H, F, Cl, Br or I; and (b) said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof provided that said at least one zeolite is not zeolite 4A. In some embodiments of this invention, the process further comprises recovering said at least one fluoroolefin having reduced concentration of said at least one $R_fC \equiv CX$ impurity.

In some embodiments of this invention, the amount of the at least one fluoroolefin in the mixture is at least 50 wt % based on the total weight of the mixture. In some embodiments of this invention, the amount of the at least one fluoroolefin in the mixture is at least 70 wt % based on the total weight of the mixture. In some embodiments of this invention, the amount of the at least one fluoroolefin in the mixture is at least 90 wt % based on the total weight of the mixture. In some embodiments of this invention, the mixture consists essentially of the at least one fluoroolefin and the at least one $R_fC \equiv CX$ impurity.

A fluoroolefin in this disclosure can be a hydrofluoroolefin or a hydrochlorofluoroolefin. In some embodiments of this invention, the at least one fluoroolefin is hydrofluoroolefin. In some embodiments of this invention, the at least one fluoroolefin is hydrochlorofluoroolefin. In some embodiments of this invention, the at least one hydrofluoroolefin is selected from the group consisting of $CF_3CF=CH_2$ (HFO-1234yf), $CF_3CH=CHF$ (HFO-1234ze), $CF_3CH=CH_2$ (HFO-1243zf), $CF_3CH=CF_2$ (HFO-1225zc), $CF_3CF=CHF$ (HFO-1225ye), and mixtures thereof. In other embodiments of this invention, the at least one hydrofluoroolefin is selected from the group consisting of $CF_3CF=CH_2$ (HFO-1234yf), $CF_3CH=CH_2$ (HFO-1243zf), $CF_3CH=CF_2$ (HFO-1225zc), $CF_3CF=CHF$ (HFO-1225ye), and mixtures thereof. In some embodiments of this invention, the at least one hydrochlorofluoroolefin is selected from the group consisting of $CF_3CCl=CH_2$ (HCFO-1233xf), $CF_3CH=CHCl$ (HCFO-1233zd), $CF_3CF=CHCl$ (HCFO-1224yd), $CF_3CH=CCl_2$ (HCFO-1223za), $CF_3CCl=CHCl$ (HCFO-1223xd), $CF_3CH=CFCl$, $CF_3CCl=CHF$, and mixtures thereof. In some embodiments of this invention, the at least one fluoroolefin is selected from the group consisting of $CF_3CF=CH_2$, $CF_3CH=CHF$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, and mixtures thereof. In other additional embodiments of this invention, the at least one fluoroolefin is selected from the group consisting of $CF_3CF=CH_2$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, and mixtures thereof. In some embodiments of this invention, the hydrofluoroolefin is at least one hydrotetrafluoropropene product selected from the group consisting of $CF_3CF=CH_2$, $CF_3CH=CHF$, and mixtures thereof. In other embodiments of this invention, the at least one fluoroolefin is $CF_3CF=CH_2$. In some embodiments of this invention, the hydrochlorofluoroolefin is at least one hydrochlorotrifluoropropene product selected from the group consisting of $CF_3CCl=CH_2$, $CF_3CH=CHCl$, and mixtures thereof.

During the processes of making fluoroolefin and its precursors, $R_fC \equiv CX$ impurities may be generated as byproducts. For example, during the dehydrochlorination process of $CF_3CFClCH_3$ (HCFC-244bb) to make HFO-1234yf, $CF_3C \equiv CH$ impurity has been found present in the product mixture with HFO-1234yf. $CF_3C \equiv CH$ impurity and/or $CF_3C \equiv CCl$ impurity may also be present in the HCFC-244bb starting material.

The $R_fC \equiv CX$ impurity that is removed from fluoroolefin by processes of this disclosure is a fluorinated terminal alkyne. In some embodiments of this invention, $R_f$ is $-CF_3$. In some embodiments of this invention, $R_f$ is $-CF_2CF_3$. In some embodiments of this invention, the at least one $R_fC \equiv CX$ impurity is selected from the group consisting of $CF_3C \equiv CH$, $CF_3C \equiv CCl$, $CF_3C \equiv CF$, and mixtures thereof. In other embodiments, the at least one $R_fC \equiv CX$ impurity is selected from the group consisting of, $CF_3C \equiv CCl$, $CF_3C \equiv CF$, and mixtures thereof. In some embodiments of this invention, the at least one $R_fC \equiv CX$ impurity is selected from the group consisting of $CF_3C \equiv CH$, $CF_3C \equiv CCl$, and mixtures thereof. In some embodiments of this invention, the at least one $R_fC \equiv CX$ impurity is $CF_3C \equiv CH$. In some embodiments of this invention, the at least one $R_fC \equiv CX$ impurity is $CF_3C \equiv CCl$.

In some embodiments of this invention, the at least one fluoroolefin is selected from the group consisting of $CF_3CF=CH_2$, $CF_3CH=CHF$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, and mixtures thereof, and the at least one $R_fC \equiv CX$ impurity is selected from the group consisting of $CF_3C \equiv CH$, $CF_3C \equiv CCl$, $CF_3C \equiv CF$, and mixtures thereof. In some embodiments of this invention, the at least one fluoroolefin is selected from the group consisting of $CF_3CF=CH_2$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, and mixtures thereof, and the at least one $R_fC \equiv CX$ impurity is selected from the group consisting of $CF_3C \equiv CH$, $CF_3C \equiv CCl$, $CF_3C \equiv CF$, and mixtures thereof. In other embodiments of this invention, the at least one fluoroolefin is selected from the group consisting of $CF_3CF=CH_2$, $CF_3CH=CHF$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, and mixtures thereof, and the at least one $R_fC\equiv CX$ impurity is selected from the group consisting of $CF_3C\equiv CCl$, $CF_3C\equiv CF$, and mixtures thereof.

In some embodiments of this invention, the at least one fluoroolefin is selected from the group consisting of $CF_3CF=CH_2$, $CF_3CH=CHF$, $CF_3CH=CH_2$, $CF_3CCl=CH_2$, $CF_3CH=CHCl$, $CF_3CF=CHCl$, and mixtures thereof, and the at least one $R_fC\equiv CX$ impurity is selected from the group consisting of $CF_3C\equiv CH$, $CF_3C\equiv CCl$, $CF_3C\equiv CF$, and mixtures thereof, while in other embodiments of this invention, the at least one fluoroolefin is selected from the group consisting of $CF_3CF=CH_2$, $CF_3CH=CH_2$, $CF_3CCl=CH_2$, $CF_3CH=CHCl$, $CF_3CF=CHCl$, and mixtures thereof, and the at least one $R_fC\equiv CX$ impurity is selected from the group consisting of $CF_3C\equiv CH$, $CF_3C\equiv CCl$, $CF_3C\equiv CF$, and mixtures thereof.

In some embodiments of this invention, the at least one fluoroolefin is $CF_3CH=CH_2$, and the at least one $R_fC\equiv CX$ impurity is selected from the group consisting of $CF_3C\equiv CH$, $CF_3C\equiv CCl$, $CF_3C\equiv CF$, and mixtures thereof.

In some embodiments of this invention, the at least one fluoroolefin is selected from the group consisting of $CF_3CF=CH_2$, $CF_3CH=CHF$, $CF_3CCl=CH_2$, $CF_3CH=CHCl$, and mixtures thereof, and the at least one $R_fC\equiv CX$ impurity is selected from the group consisting of $CF_3C\equiv CH$, $CF_3C\equiv CCl$, and mixtures thereof. In some embodiments of this invention, the at least one fluoroolefin is selected from the group consisting of $CF_3CF=CH_2$, $CF_3CCl=CH_2$, $CF_3CH=CHCl$, and mixtures thereof, and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is selected from the group consisting of $CF_3CF=CH_2$, $CF_3CH=CHF$, $CF_3CCl=CH_2$, $CF_3CH=CHCl$, and mixtures thereof, and the at least one $R_fC\equiv CX$ impurity is $CF_3C\equiv CH$. In some embodiments of this invention, the at least one fluoroolefin is selected from the group consisting of $CF_3CF=CH_2$, $CF_3CCl=CH_2$, $CF_3CH=CHCl$, and mixtures thereof, and the at least one $R_fC\equiv CX$ impurity is $CF_3C\equiv CH$.

In some embodiments of this invention, the at least one fluoroolefin is $CF_3CF=CH_2$, and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is $CF_3CF=CH_2$, and the at least one $R_fC\equiv CX$ impurity is $CF_3C\equiv CH$.

In some embodiments of this invention, the at least one fluoroolefin is $CF_3CH=CHF$, and the at least one $R_fC\equiv CX$ impurity is selected from the group consisting of $CF_3C\equiv CH$, $CF_3C\equiv CCl$, and mixtures thereof. In some embodiments, the at least one fluoroolefin is $CF_3CH=CHF$, and the at least one $R_fC\equiv CX$ impurity is selected from the group consisting of $CF_3C\equiv CH$, $CF_3C\equiv CCl$, and mixtures thereof, wherein said at least one zeolite comprises a zeolite having pore opening of at least about 5 Angstroms and Sanderson electronegativity of no more than about 2.6, or combination thereof.

In some embodiments of this invention, the at least one fluoroolefin is $CF_3CH=CHF$, and the at least one $R_fC\equiv CX$ impurity is $CF_3C\equiv CH$. In other embodiments, the at least one fluoroolefin is $CF_3CH=CHF$, and the at least one $R_fC\equiv CX$ impurity is $CF_3C\equiv CH$ and at least one zeolite comprises a zeolite having pore opening of at least about 5 Angstroms and Sanderson electronegativity of no more than about 2.6, or combination thereof.

In some embodiments of this invention, the at least one fluoroolefin is a mixture of $CF_3CF=CH_2$ and $CF_3CH=CHF$, and the at least one $R_fC\equiv CX$ impurity is selected from the group consisting of $CF_3C\equiv CH$, $CF_3C\equiv CCl$, and mixtures thereof. In other embodiments of this invention, the at least one fluoroolefin is a mixture of $CF_3CF=CH_2$ and $CF_3CH=CHF$, and the at least one $R_fC\equiv CX$ impurity is selected from the group consisting of $CF_3C\equiv CH$, $CF_3C\equiv CCl$, and mixtures thereof, and the at least one zeolite is selected from the group consisting of zeolites having pore opening of at least about 5 Angstroms and Sanderson electronegativity of no more than about 2.6, and mixtures thereof. In some embodiments of this invention, the at least one fluoroolefin to be produced is $CF_3CF=CH_2$ and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is a mixture of $CF_3CF=CH_2$ and $CF_3CH=CHF$, and the at least one $R_fC\equiv CX$ impurity is $CF_3C\equiv CH$. In other embodiments of the present invention, the at least one fluoroolefin is $CF_3CF=CH_2$, and the at least one $R_fC\equiv CX$ impurity is $CF_3C\equiv CH$. In other embodiments, the at least one fluoroolefin is a mixture of $CF_3CF=CH_2$ and $CF_3CH=CHF$, and the at least one $R_fC\equiv CX$ impurity is $CF_3C\equiv CH$ and at least one zeolite comprises a zeolite having pore opening of at least about 5 Angstroms and Sanderson electronegativity of no more than about 2.6, or combination thereof.

In some embodiments of this invention, the at least one fluoroolefin is selected from the group consisting of $CF_3CCl=CH_2$, $CF_3CH=CHCl$, and mixtures thereof, and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is selected from the group consisting of $CF_3CCl=CH_2$, $CF_3CH=CHCl$, and mixtures thereof, and the at least one $R_fC\equiv CX$ impurity is $CF_3C\equiv CH$.

In some embodiments of this invention, the at least one fluoroolefin is $CF_3CH=CHCl$, and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is $CF_3CH=CHCl$, and the at least one $R_fC\equiv CX$ impurity is $CF_3C\equiv CH$.

In some embodiments of this invention, the at least one fluoroolefin is $CF_3CCl=CH_2$, and the at least one $R_fC\equiv CX$ impurity is selected from the group consisting of $CF_3C\equiv CH$, $CF_3C\equiv CCl$, and mixtures thereof.

In some embodiments of this invention, the at least one fluoroolefin is $CF_3CCl=CH_2$, and the at least one $R_fC\equiv CX$ impurity is $CF_3C\equiv CH$.

It has been found through experiments that $R_fC\equiv CX$ impurity can be removed from fluoroolefin by contacting with a zeolite selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof provided that said at least one zeolite is not zeolite 4A. In other embodiments, the zeolites utilized have pore openings of at least 4 Angstroms and no more than about 5 Angstroms, or combination of more than one thereof, while in other embodiments, the zeolite used is the zeolite having pore opening of at least about 5 Angstroms and Sanderson electronegativity of no more than about 2.6, and combination thereof or the zeolite utilized is a mixture of at least one zeolite having pore openings of at least 4 Angstroms and no more than about 5 Angstroms and at least one zeolite having pore opening of at least about 5 Angstroms and Sanderson electronegativity of no more than about 2.6.

The contacting step of this disclosure can be carried out using well-known chemical engineering practices for scrubbing organic compounds, which includes continuous, semi-continuous or batch operations. In some embodiments of this invention, the contacting step can be carried out by passing a gaseous or liquid mixture of fluoroolefin and $R_fC\equiv CX$ impurity through a bed of zeolite. Stirring and agitation of the bed may be carried out through use of known methods. In some embodiments of this invention, fluoroolefin containing $R_fC\equiv CX$ impurity is mixed with zeolite in a vessel equipped with an agitator.

In some embodiments of this invention, the temperature during the contacting step is from about −20° C. to about 200° C. In some embodiments of this invention, the temperature during the contacting step is from about 0° C. to about 100° C. In some embodiments of this invention, the temperature during the contacting step is from about 10° C. to about 60° C. In some embodiments of this invention, the temperature during the contacting step is about room temperature. The pressure during the contacting step is not critical and can be in the range of from about 10 kPa to about 3000 kPa.

During the contacting step, the mixture of fluoroolefin and $R_fC\equiv CX$ impurity is scrubbed with zeolite in the contacting vessel, and the $R_fC\equiv CX$ impurity is removed. In some embodiments of this invention, the concentration of the at least one $R_fC\equiv CX$ impurity in the mixture is reduced to 300 ppm or less. In some embodiments of this invention, the concentration of the at least one $R_fC\equiv CX$ impurity in the mixture is reduced to 200 ppm or less. In some embodiments of this invention, the concentration of the at least one $R_fC\equiv CX$ impurity in the mixture is reduced to 100 ppm or less. In some embodiments of this invention, the amount of the at least one $R_fC\equiv CX$ impurity in the mixture is reduced at least about 20% by weight relative to the amount originally present. In some embodiments of this invention, the amount of the at least one $R_fC\equiv CX$ impurity in the mixture is reduced at least about 30% by weight relative to the amount originally present. In some embodiments of this invention, the amount of the at least one $R_fC\equiv CX$ impurity in the mixture is reduced at least about 45% by weight relative to the amount originally present.

The fluoroolefin having reduced concentration of the $R_fC\equiv CX$ impurity obtained from the contacting step can be recovered using techniques well-known in the art, such as condensation or distillation. In some embodiments of this invention, the fluoroolefin obtained from the contacting step may be further purified by fractional distillation.

Zeolites with sorbed $R_fC\equiv CX$ impurity can be regenerated by desorption of the $R_fC\equiv CX$ impurity and other sorbed components (if present). Desorption may be effected with or without the use of a purge liquid or gas flow. In some embodiments of this invention, the desorption is carried out at an elevated temperature with a purge gas such as air or nitrogen.

In general, desorption can be effected by changing any thermodynamic variable which is effective in removing the sorbed components (i.e., $R_fC\equiv CX$ impurity and other sorbed components if also present) from the zeolite. For example, sorption and desorption may be effected using a thermal swing cycle (e.g., where after a period of sorption, the zeolite is heated such that sorbed components are desorbed); or using a pressure swing cycle or vacuum swing cycle (e.g., where after a period of sorption, the pressure is reduced such that sorbed components are desorbed). The thermal swing cycle and the pressure swing cycle or vacuum swing cycle can be combined.

The present disclosure also provides a process for making at least one hydrotetrafluoropropene product selected from the group consisting of $CF_3CF=CH_2$, $CF_3CH=CHF$, and mixtures thereof. The process comprises: (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CH_2F$, $CF_3CF_2CH_3$, and mixtures thereof to produce a product mixture comprising $CF_3C\equiv CH$ impurity and said at least one hydrotetrafluoropropene product; (b) contacting said product mixture with at least one zeolite to reduce the concentration of said $CF_3C\equiv CH$ impurity in said product mixture; and (c) recovering said at least one hydrotetrafluoropropene product having reduced concentration of said $CF_3C\equiv CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof provided that said at least one zeolite is not zeolite 4A. In another embodiment, the present disclosure also provides a process for making at least one hydrotetrafluoropropene product selected from the group consisting of $CF_3CF=CH_2$, $CF_3CH=CHF$, and mixtures thereof, wherein the process comprises: (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CF_2H$, $CF_3CF_2CH_3$, and mixtures thereof to produce a product mixture comprising $CF_3C\equiv CH$ impurity and said at least one hydrotetrafluoropropene product; (b) contacting said product mixture with at least one zeolite to reduce the concentration of said $CF_3C\equiv CH$ impurity in said product mixture; and (c) recovering said at least one hydrotetrafluoropropene product having reduced concentration of said $CF_3C\equiv CH$ impurity; wherein said at least one zeolite is selected from the group consisting of zeolites having pore opening of at least about 5 Angstroms and Sanderson electronegativity of no more than about 2.6, and mixtures thereof. In still another embodiment, the present disclosure also provides a process for making $CF_3CF=CH_2$, which process comprises: (a) dehydrohalogenating at least one starting material selected from the group consisting of $CF_3CFClCH_3$, $CF_3CHFCH_2Cl$, $CF_3CHFCH_2F$, $CF_3CF_2CH_3$, and mixtures thereof to produce a product mixture comprising $CF_3C\equiv CH$ impurity and said at least one hydrotetrafluoropropene product; (b) contacting said product mixture with at least one zeolite to reduce the concentration of said $CF_3C\equiv CH$ impurity in said product mixture; and (c) recovering said at least one hydrotetrafluoropropene product having reduced concentration of said $CF_3C\equiv CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A.

The present disclosure also provides a process for making at least one hydrochlorotrifluoropropene product selected from the group consisting of $CF_3CCl=CH_2$, $CF_3CH=CHCl$, and mixtures thereof. The process comprises: (a) dehydrohalogenating at least one starting material selected from the group consisting of $CF_3CCl_2CH_3$, $CF_3CHClCH_2Cl$, $CF_3CHClCH_2F$, $CF_3CH_2CHCl_2$, $CF_3CHFCH_2Cl$, $CF_3CFClCH_3$, $CF_3CH_2CHFCl$, and mixtures thereof to produce a product mixture comprising $CF_3C\equiv CH$ impurity and said at least one hydrochlorotrifluoropropene product; (b) contacting said product mixture with at least one zeolite to reduce the concentration of said $CF_3C\equiv CH$ impurity in said product mixture; and (c) recovering said at least one hydrochlorotrifluoropropene product having reduced concentration of said $CF_3C\equiv CH$ impurity; wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A.

In some embodiments of this invention, the dehydrohalogenation process is carried out by pyrolyzing (thermally dehydrohalogenating) the starting material to produce the hydrotetrafluoropropene or hydrochlorotrifluoropropene product. The term "pyrolyzing" or "pyrolysis", as used herein, means chemical change produced by heating in the absence of catalyst. By absence of catalyst is meant that no material or treatment is added to the pyrolysis reactor that increases the reaction rate by reducing the activation energy of the pyrolysis process.

Suitable reactors for pyrolysis may be of any shape consistent with the process. In some embodiments of this invention, the reactor is a cylindrical tube, either straight or coiled. Heat is applied to the outside of the tube, with the chemical reaction taking place on the inside of the tube. Of note are pyrolysis reactors wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, has an open structure like that of Raschig Rings or other packings with a high free volume to avoid the accumulation of coke and to minimize pressure drop, and permits a generally free flow of gas. In some embodiments of this invention, the reactor packing is in cartridge disposition for ease of insertion and removal. In some embodiments of this invention, the pyrolysis reactor is substantially empty which means that the free volume of the reaction zone is at least about 80%, and in another embodiment, at least about 90%, and in another embodiment at least about 95%. The free volume is the volume of the reaction zone minus the volume of the material that makes up the reactor packing, and the % free volume is the ratio of the free volume relative to the total volume of the reactor times 100.

In some embodiments of this invention, the pyrolysis reactor is comprised of materials which are resistant to corrosion including stainless steel, Hastelloy™, Inconel™, Monel™, gold, or gold-lined or quartz.

The dehydrohalogenation process of this disclosure can be either a dehydrofluorination process or a dehydrochlorination process depending on the starting material and the corresponding fluoroolefin product. Typically, the pyrolysis temperature for dehydrofluorination is higher than the one for dehydrochlorination. In some embodiments of this invention, the dehydrofluorinating pyrolysis is conducted at a temperature of from about 600° C. to about 900° C. In some embodiments of this invention, the dehydrochlorinating pyrolysis is conducted at a temperature of from about 400° C. to about 700° C. Pyrolysis processes have also been disclosed in U.S. Pat. No. 7,833,434, U.S. Patent Publication No. 2010-0105967, and U.S. Patent Publication No. 2010-0105967.

In some embodiments of this invention, the dehydrohalogenation process is carried out in the presence of a catalyst. Suitable catalysts for dehydrohalogenation include alumina, fluorided alumina, aluminum fluoride, aluminum chlorofluoride; metal compounds supported on alumina, fluorided alumina, aluminum fluoride, or aluminum chlorofluoride; chromium oxide ($Cr_2O_3$), fluorided chromium oxide, and cubic chromium trifluoride; oxides, fluorides, and oxyfluorides of magnesium, zinc and mixtures of magnesium and zinc and/or aluminum; lanthanum oxide and fluorided lanthanum oxide; carbon, and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. In some embodiments of this invention, the dehydrohalogenation catalyst is selected from the group consisting of carbon, alumina, fluorided alumina, and mixtures thereof. In some embodiments of this invention, carbon includes acid-washed carbon, activated carbon and three dimensional matrix carbonaceous materials. In some embodiments of this invention, the dehydrohalogenation catalyst comprises alkali metal salt supported on chromium oxide. The catalytic dehydrohalogenation processes have also been disclosed in U.S. Pat. Nos. 7,943,015, 7,897,823, and 7,985,884.

In some embodiments of this invention, the dehydrohalogenation process is carried out by reacting the starting material with a basic aqueous solution to produce the hydrotetrafluoropropene or hydrochlorotrifluoropropene product. As used herein, the basic aqueous solution is a liquid that is primarily an aqueous liquid having a pH of over 7, and the liquid may be a solution, dispersion, emulsion, suspension or the like. In some embodiments of this invention, the basic aqueous solution has a pH of 8 or higher. In some embodiments of this invention, the basic aqueous solution has a pH of 10 or higher. Typically, a dehydrofluorination process needs a higher pH solution than a dehydrochlorination process.

In embodiments of this invention, an inorganic base is used to form the basic aqueous solution. Such inorganic base can be selected from the group consisting of hydroxide, oxide, carbonate, and phosphate salts of alkali, alkaline earth metals and mixtures thereof. In some embodiments, such inorganic base is sodium hydroxide, potassium hydroxide, or mixtures thereof. In some embodiments of this invention, the basic aqueous solution is an aqueous solution of a quaternary ammonium hydroxide of the formula $NR_4OH$ wherein each R is independently hydrogen, a $C_1$ to $C_{16}$ alkyl group, aralkyl group, or substituted alkyl group, provided that not all R are hydrogens. Examples of $NR_4OH$ compounds include tetra-n-butylammonium hydroxide, tetra-n-propylammonium hydroxide, tetraethyl ammonium hydroxide, tetramethylammonium hydroxide, benzyltrimethylammonium hydroxide, hexadecyltrimethylammonium hydroxide, choline hydroxide, and mixtures thereof.

Optionally, the starting material is reacted with the basic aqueous solution in the presence of an organic solvent. In some embodiments of this invention, the organic solvent is selected from the group consisting of benzene and its derivatives, alcohols, alkyl halides, alkyl nitriles, ethers, amides, ketones, sulfoxides, phosphate esters and mixtures thereof.

Optionally, the starting material is reacted with the basic aqueous solution in the presence of a phase transfer catalyst. As used herein, the term "phase transfer catalyst" is intended to mean a substance that facilitates the transfer of ionic compounds into an organic phase from an aqueous phase or from a solid phase. A phase transfer catalyst facilitates the reaction between water-soluble and water-insoluble reaction components. In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral. In some embodiments of this invention, onium salts include quaternary phosphonium salts and quaternary ammonium salts. Examples of quaternary ammonium salts include tetra-n-butylammonium hydroxide, tetramethylammonium chloride, tetramethylammonium bromide, benzyltriethylammonium chloride, methyltri-n-octyl ammonium chloride (also known as Aliquat™ 336), dodecyltrimethylammonium bromide, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide, triphenylmethylphosphonium chloride, and mixtures thereof.

The dehydrohalogenation using a basic aqueous solution has also been disclosed in PCT Publication No. WO2010/129844.

In some embodiments of this invention, during the dehydrohalogenating step, starting materials selected from the group consisting of $CF_3CFClCH_3$ (HCFC-244bb), $CF_3CHFCH_2Cl$ (HCFC-244eb), $CF_3CHClCH_2F$ (HCFC-244db), $CF_3CH_2CHFCl$ (HCFC-244fa), $CF_3CHFCH_2F$ (HFC-245eb), $CF_3CH_2CF_2H$ (HFC-245fa), and $CF_3CF_2CH_3$ (HFC-245cb) are dehydrohalogenated to form either $CF_3CF=CH_2$ or $CF_3CH=CHF$ product. In other embodiments of this invention, during the dehydrohalogenating step, starting materials selected from the group consisting of $CF_3CFClCH_3$ (HCFC-244bb), $CF_3CHFCH_2F$ (HFC-245eb), and $CF_3CF_2CH_3$ (HFC-245cb) are dehydrohalogenated to form $CF_3CF=CH_2$. In some embodiments of this invention, the at least one starting material is selected from the group consisting of $CF_3CFClCH_3$, $CF_3CHFCH_2Cl$, $CF_3CHFCH_2F$, $CF_3CF_2CH_3$, and mixtures thereof, and the at least one hydrotetrafluoropropene product is $CF_3CF=CH_2$. In some embodiments of this invention, the at least one starting material is $CF_3CFClCH_3$, and the at least one hydrotetrafluoropropene product is $CF_3CF=CH_2$ (i.e., the starting material $CF_3CFClCH_3$ is dehydrochlorinated to produce a product mixture comprising $CF_3CF=CH_2$ product and $CF_3C\equiv CH$ impurity). In some embodiments of this invention, the at least one starting material is $CF_3CHFCH_2F$, and the at least one hydrotetrafluoropropene product is $CF_3CF=CH_2$ (i.e., the starting material $CF_3CHFCH_2F$ is dehydrofluorinated to produce a product mixture comprising $CF_3CF=CH_2$ product and $CF_3C\equiv CH$ impurity). In some embodiments of this invention, the at least one starting material is selected from the group consisting of $CF_3CH_2CHF_2$, $CF_3CH_2CHFCl$, $CF_3CHClCH_2F$, and mixtures thereof, and the at least one hydrotetrafluoropropene product is $CF_3CH=CHF$. In an embodiment, the at least one starting material is selected from the group consisting of $CF_3CH_2CHF_2$, $CF_3CH_2CHFCl$, $CF_3CHClCH_2F$, and mixtures thereof, and the at least one hydrotetrafluoropropene product is $CF_3CH=CHF$ and the zeolite utilized comprises zeolite having pore opening of at least about 5 Angstroms and Sanderson electronegativity of no more than about 2.6, and mixtures thereof In some embodiments of this invention, during the dehydrohalogenating step, starting materials selected from the group consisting of $CF_3CCl_2CH_3$ (HCFC-243ab), $CF_3CHClCH_2Cl$ (HCFC-243db), $CF_3CHClCH_2F$ (HCFC-244db), $CF_3CH_2CHCl_2$ (HCFC-243fa), $CF_3CHFCH_2Cl$ (HCFC-244eb), $CF_3CFClCH_3$ (HCFC-244bb), and $CF_3CH_2CHFCl$ (HCFC-244fa) are dehydrohalogenated to form either $CF_3CCl=CH_2$ or $CF_3CH=CHCl$ product. In some embodiments of this invention, the at least one starting material is selected from the group consisting of $CF_3CHClCH_2Cl$, $CF_3CH_2CHCl_2$, and mixtures thereof, and the at least one hydrochlorotrifluoropropene product is $CF_3CH=CHCl$ (i.e., the at least one starting material selected from the group consisting of $CF_3CHClCH_2Cl$, $CF_3CH_2CHCl_2$, and mixtures thereof is dehydrochlorinated to produce a product mixture comprising $CF_3CH=CHCl$ product and $CF_3C\equiv CH$ impurity). In some embodiments of this invention, the at least one starting material is selected from the group consisting of $CF_3CHClCH_2Cl$, $CF_3CCl_2CH_3$, and mixtures thereof, and the at least one hydrochlorotrifluoropropene product is $CF_3CHCl=CH_2$ (i.e., the at least one starting material selected from the group consisting of $CF_3CHClCH_2Cl$, $CF_3CCl_2CH_3$, and mixtures thereof is dehydrochlorinated to produce a product mixture comprising $CF_3CHCl=CH_2$ product and $CF_3C\equiv CH$ impurity).

During the dehydrohalogenating step, alkyne byproduct, such as $CF_3C\equiv CH$ is also generated. During the contacting step, the product mixture of hydrotetrafluoropropene or hydrochlorotrifluoropropene product and the alkyne impurity, such as $CF_3C\equiv CH$ impurity is scrubbed with the suitable zeolite as described in this disclosure by using the contacting step processes as also described in this disclosure.

In some embodiments of this invention, the concentration of the alkyne impurity, such as $CF_3C\equiv CH$ is reduced to 300 ppm or less in the contacting step (b). In some embodiments of this invention, it is reduced to 200 ppm or less. In some embodiments of this invention, it is reduced to 100 ppm or less. In some embodiments of this invention, the amount of the alkyne impurity, e.g., $CF_3C\equiv CH$ impurity, in the hydrotetrafluoropropene or hydrochlorotrifluoropropene product mixture is reduced in the contacting step by at least about 20% by weight relative to the amount originally present. In some embodiments of this invention, it is reduced at least about 30% by weight relative to the amount originally present. In some embodiments of this invention, it is reduced at least about 45% by weight relative to the amount originally present.

In some embodiments of this invention, the concentration of the alkyne impurity, e.g., $CF_3C\equiv CH$ impurity, in the product mixture comprising $CF_3C\equiv CH$ impurity and $CF_3CF=CH_2$ product is reduced to 300 ppm or less in the contacting step (b). In some embodiments of this invention, it is reduced to 200 ppm or less. In some embodiments of this invention, it is reduced to 100 ppm or less. In some embodiments of this invention, the amount of the alkyne impurity, e.g., $CF_3C\equiv CH$ impurity, in the product mixture comprising $CF_3C\equiv CH$ impurity and $CF_3CF=CH_2$ product is reduced in the contacting step (b) by at least about 20% by weight relative to the amount originally present. In some embodiments of this invention, it is reduced at least about 30% by weight relative to the amount originally present. In some embodiments of this invention, it is reduced at least about 45% by weight relative to the amount originally present.

In some embodiments of this invention, the concentration of the alkyne, e.g., $CF_3C{\equiv}CH$ impurity, in the product mixture comprising $CF_3C{\equiv}CH$ impurity and $CF_3CH{=}CHF$ product is reduced to 300 ppm or less in the contacting step (b). In some embodiments of this invention, it is reduced to 200 ppm or less. In some embodiments of this invention, it is reduced to 100 ppm or less. In some embodiments of this invention, the amount of the alkyne impurity, e.g., $CF_3C{\equiv}CH$ impurity, in the product mixture comprising $CF_3C{\equiv}CH$ impurity and $CF_3CH{=}CHF$ product is reduced in the contacting step (b) by at least about 20% by weight relative to the amount originally present. In some embodiments of this invention, it is reduced at least about 30% by weight relative to the amount originally present. In some embodiments of this invention, it is reduced at least about 45% by weight relative to the amount originally present.

The hydrotetrafluoropropene or hydrochlorotrifluoropropene product obtained from the contacting step (b) can be recovered using the recovering step processes as described in this disclosure. In some embodiments of this invention, various azeotropic or azeotrope-like (i.e., near azeotrope) compositions of the hydrotetrafluoropropene or hydrochlorotrifluoropropene product may be utilized in the processes of recovering these products. For example, HF can be added to the HFO-1234yf product mixture obtained from the contacting step (b), and separation of HFO-1234yf includes isolation of azeotrope or near azeotrope of HFO-1234yf and HF and subjecting the azeotrope or near azeotrope of HFO-1234yf and HF to further processing to produce HF-free HFO-1234yf by using procedures similar to that disclosed in U.S. Pat. No. 7,897,823. Azeotrope or near azeotrope compositions of HFO-1234yf and HF have been disclosed in U.S. Pat. No. 7,476,771, and the process described therein may also be utilized for recovering the hydrotetrafluoropropene or hydrochlorotrifluoropropene product. For another example, HF can be added to the HFO-1234ze product mixture obtained from the contacting step (b), and separation of HFO-1234ze includes isolation of azeotrope or near azeotrope of HFO-1234ze and subjecting the azeotrope or near azeotrope of HFO-1234ze and HF to further processing to produce HF-free HFO-1234ze by using procedures similar to that disclosed in U.S. Pat. No. 7,897, 823. U.S. Pat. No. 7,423,188 discloses azeotrope or near-azeotrope compositions of the E-isomer of HFO-1234ze and HF, and U.S. Patent Publication No. 2010-0200798 discloses azeotrope or near-azeotrope compositions of the Z-isomer of HFO-1234ze and HF, and the techniques applied therein may be utilized to recover HF-free HFO-1234ze. For another example, HF can be added to the HCFO-1233xf product mixture obtained from the contacting step (b), and separation of HCFO-1233xf includes isolation of azeotrope or near azeotrope of HCFO-1233xf and HF and subjecting the azeotrope or near azeotrope of HFO-1234xf and HF to further processing to produce HF-free HCFO-1233xf by using procedures similar to that disclosed in U.S. Pat. No. 7,897,823. The azeotrope compositions of HCFO-1233xf and HF has been disclosed in U.S. Patent Publication No. 2010-0072415, and the techniques for recovering HF-free HCFO-1233xf are applicable for recovering. For another example, HF can be added to the HCFO-1233zd product mixture obtained from the contacting step (b), and separation of HCFO-1233zd includes isolation of azeotrope or near azeotrope of HCFO-1233zd and HF and HF-free HCFO-1233zd and subjecting the azeotropic HF-free HCFO-1233xf to further processing to produce HF-free HCFO-1233zd by using procedures similar to that disclosed in U.S. Pat. No. 7,897,823. Some azeotrope compositions of HCFO-1233zd and HF have been disclosed in U.S. Pat. No. 6,013,846, and the techniques utilized therein may be utilized to recover HCFO-1233zd.

The contacting vessels, reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Suitable Zeolites of this Disclosure:

Zeolites used in the processes of this invention are crystalline, highly porous materials. They can be generically described as complex aluminosilicates characterized by a three-dimensional pore system. The zeolite framework structure has corner-linked tetrahedra with Al or Si atoms at centers of the tetrahedra and oxygen atoms at the corners. In order to be a zeolite, the ratio (Si+Al)/O must equal ½. Such tetrahedra are combined in a well-defined repeating structure comprising various combinations of 4-, 6-, 8-, 10-, and 12-membered rings. The resulting framework structure is one of regular channels and/or cages, which has a pore network that is useful for separation or purification purposes. The size of pore opening is critical to the performance of zeolite in separation or purification applications, since this characteristic determines whether molecules of certain size can enter and exit the zeolite pore system.

The size of the pore opening that controls access to the interior of the zeolites is determined not only by the geometric dimensions of the tetrahedra forming the pore opening, but also by the presence or absence of ions in or near the pore. For example, in the case of zeolite A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit pore openings of about 3 Angstroms and about 4 Angstroms respectively, whereas the calcium salt of zeolite A has a pore opening of about 5 Angstroms.

The Sanderson electronegativity model (see R. T. Sanderson, "Chemical Bonds and Bond Energy", $2^{nd}$ ed., Academic Press, New York, 1976 (i.e., Sanderson 1976 model); R. T. Sanderson, "Electronegativity and Bond Energy", J. Amer. Chem. Soc. 1983, 105, 2259-2261 (i.e., Sanderson 1983 model); W. J. Mortier, "Zeolite Electronegativity Related to Physicochemical Properties", J. Catal. 1978, 83, 138-145) furnishes a useful method for classifying zeolites based on their chemical composition. In accordance with this invention the preferential sorption of $R_fC{\equiv}CX$ impurity by zeolites can be correlated with their intermediate electronegativity (i.e., their $S_{int}$, the geometric mean of the electronegativities) as determined by the Sanderson method based upon chemical composition. According to Barthomeuf (D. Barthomeuf, "Acidity and Basicity in Zeolites", In Catalysis and Adsorption in Zeolites, G. Ohlmann et al., eds., Elsevier (1991), pages 157-169), an apparent $S_{int}$ break point between acidity and basicity is at about 3.5 (based on Sanderson 1976 model) or about 2.6 (based on Sanderson 1983 model). In other words, generally, zeolites with $S_{int}$ of no more than about 2.6 (based on Sanderson 1983 model)

tend to exhibit base properties, while those with $S_{int}$ greater than about 2.6 are acidic. The term "Sanderson electronegativity", as used herein, refers to the $S_{int}$ value based on Sanderson 1983 model.

Zeolites suitable for use in the processes of this invention are selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof. Suitable zeolites in this disclosure do not include zeolite 4A.

Suitable zeolites include those having a pore opening of about 4.1, 4.2, 4.3, 4.4, 4.5, 4.6, 4.7, 4.8, 4.9, 5.0, or 5.1 Angstroms.

Suitable zeolites also include those having a Sanderson electronegativity of no more than about 2.61, 2.60, 2.59, 2.58, 2.57, 2.56, 2.55, 2.54, 2.53, 2.52, 2.51, 2.50, 2.49, 2.48, 2.47, 2.46, 2.45, 2.44, 2.43, 2.42, 2.41, 2.40, 2.39, or 2.38.

In some embodiments of this invention, zeolites have a Sanderson electronegativity of no more than about 2.56. In some embodiments of this invention, zeolites have a Sanderson electronegativity of no more than about 2.38.

In some embodiments of this invention, zeolites have a pore opening of at least 4 Angstroms and no more than about 5 Angstroms. These zeolites are not restricted to those zeolites having a Sanderson electronegativity of no more than about 2.6. However, in an embodiment, the zeolites have a pore opening of at least 4 Angstroms and no more than about 5 Angstroms and a Sanderson electronegativity of no more than about 2.6.

In some embodiments of this invention, zeolites have a pore opening of at least about 5 Angstroms and have a Sanderson electronegativity of no more than about 2.6.

In some embodiments of this invention, zeolites have a pore opening of at least about 5 Angstroms and have a Sanderson electronegativity of no more than about 2.56.

In some embodiments of this invention, zeolites are selected from the group consisting of zeolite 5A, zeolite 13X, zeolite LSX, zeolite AW-300, zeolite AW-500, and mixtures thereof.

In some embodiments of this invention, zeolites are selected from the group consisting of zeolite 5A, zeolite 13X, zeolite AW-300, zeolite AW-500, and mixtures thereof.

In some embodiments of this invention, zeolites are selected from the group consisting of zeolite 5A, zeolite 13X, and mixtures thereof.

In some embodiments of this invention, zeolites are selected from the divalent cation forms of zeolite A, such as $Ca^{2+}$, $Sr^{2+}$, $Ba^{2+}$, $Cd^{2+}$, and $Zn^{2+}$.

Mixtures of any of the aforementioned zeolites may also be used in practicing this invention.

Zeolites are typically pre-treated before use by heating, optionally in a dry gas stream. The pre-treatment temperature is typically in the range of from about 100° C. to about 550° C. The dry gas stream is typically dry air or dry nitrogen.

This invention can be practiced with the zeolite or molecular sieve contained in a stationary packed bed through which the process stream whose components need separation are passed. Alternatively, it can be practiced with the zeolite or molecular sieve applied as a countercurrent moving bed; or with a fluidized bed where the sorbent itself is moving. It can be applied with the zeolite or molecular sieve contained as a stationary packed bed, but the process configured as a simulated moving bed, where the point of introduction to the bed of the process stream requiring separation is changed, such as may be effected using appropriate switching valves.

EXAMPLE OF USE OF PRESENT INVENTION

The removal of $CF_3C\equiv CH$ impurity from the final product, namely HFO-1234yf using techniques known in the art heretofore, will incur extra cost and possibly yield loss as well. But, the present invention provides methods of removing $CF_3C\equiv CH$ from the reactor feed to improve the overall efficiency of the HFO-1234yf conversion process.

An aspect of the present invention is the preparation of HFO-1234yf that is substantially free of 3,3,3-trifluoropropyne comprising:

(i) providing a starting composition including a compound of Formulae I, II, or III:

$$CX_2=CCl-CH_2X \quad (I);$$

$$CX_3-CCl=CH_2 \quad (II); \text{ or}$$

$$CX_3-CHCl-CH_2X \quad (III)$$

wherein X is independently selected from F, Cl, Br, and I, provided that at least one X is not fluorine;

(ii) contacting the starting composition with a first fluorinating agent to produce a first intermediate composition including 2-chloro-3,3,3-trifluoropropene and a first chlorine-containing byproduct;

(iii) contacting the first intermediate composition with a second fluorinating agent to produce a second intermediate composition including 2-chloro-1,1,1,2-tetrafluoropropane and 2-chloro-3,3,3-trifluoropropene;

(iv) dehydrochlorinating at least a portion of the second intermediate composition including 2-chloro-1,1,1,2-tetrafluoropropane and 2-chloro-3,3,3-trifluoropropene to produce a reaction product including 2,3,3,3-tetrafluoropropene and $CF_3C\equiv CH$ impurity;

(v) contacting the product of step iv with at least one zeolite, wherein said at least one zeolite is selected from the group consisting of zeolites having pore opening of at least 4 Angstroms and no more than about 5 Angstroms, zeolites having pore opening of at least about 5 Angstroms and Sanderson electronegativity of no more than about 2.6, and mixtures thereof; provided that said at least one zeolite is not zeolite 4A, to provide 2,3,3,3-tetrafluoropropene, said reaction product being substantially free of said $CF_3C\equiv CH$ impurity; and (vi) recovering said 2,3,3,3-tetrafluoropropene produced in step (v) having reduced concentration of said $CF_3C\equiv CH$ impurity.

In certain aspects, the preparation of HFO-1234yf generally includes at least three reaction steps, as follows:

(1) $(CX_2=CCl-CH_2X$ or $CX_3-CCl=CH_2$ or $CX_3-CHCl-CH_2X)+HF \rightarrow$ 2-chloro-3,3,3-trifluoropropene (HCFO-1233xf)+HCl in a vapor phase reactor charged with a solid catalyst;

(2) 2-chloro-3,3,3-trifluoropropene (HCFO-1233xf)+ HF$\rightarrow$2-chloro-1,1,1,2-tetrafluoropropane (HCFC-244bb) in a liquid phase reactor charged with a liquid hydrofluorination catalyst; and (3) 2-chloro-1,1,1,2-tetrafluoropropane (HCFC-244bb) $\rightarrow$2,3,3,3-tetrafluoropropene (HFO-1234yf) in a vapor phase reactor.

wherein X is independently selected from F, Cl, Br, and I, provided that at least one X is not fluorine.

Generally speaking, the starting material of the first reaction step may be represented by one or more chlorinated compounds according to Formulas I, II, and/or III:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br, and I, provided that at least one X is not fluorine. In certain embodiments, these compounds contain at least one chlorine, a majority of X is chlorine, or all X is chlorine.

In the first step, such starting materials (which, in certain embodiments includes 1,1,2,3-tetrachloropropene (1230 xa) and/or 1,1,1,2,3-pentachloropropane (HCC-240db)) is reacted with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, heavy intermediates, HCFC-244bb, HFC-245cb (1,1,1,2,2-pentafluoropropane), or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. Chromium (III) oxides such as crystalline chromium oxide or amorphous chromium oxide are suitable catalysts and in an embodiment, the catalyst used in this step is amorphous chromium oxide. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction, as described above, but may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuously, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_4$, $SnCl_4$, $TiCl_4$, $FeCl_3$ and combinations of two or more of these.

The effluent from the reactor may be optionally processed to achieve desired degrees of separation and/or other processing. By way of non-limiting example, the product effluent may contain one or more impurities, such as, HCl, unconverted reactants, and/or other by-products. These products may be removed using standard methods known or otherwise discussed herein. HCl, for example, can be recovered by conventional distillation, or using water or caustic scrubbers, as discussed in greater detail below, and the unreacted starting reagents isolated and recycled.

In the second step of the process for forming 2,3,3,3-tetrafluoropropene, HCFO-1233xf is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reactor can either be non-catalytic or it can contain a catalyst that can catalytically dehydrochlorinate HCFC-244bb to make HFO-1234yf.

The catalysts, if present, may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, Br2, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Incoloy 825, Alloy 20, Hastelloy, Inconel 600, and Inconel 625.

In an aspect of the present invention, in this step, catalysts include activated carbon, stainless steel (e.g., SS 316), austenitic nickel-based alloys (e.g., Inconel 625), nickel, and in certain embodiments fluorinated 10% CsCl/MgO. A suitable reaction temperature is about 300-550° C. and a suitable reaction pressure may be between about 0-150 psig. The reactor effluent may be fed to a caustic scrubber or to a distillation column to remove the byproduct of HCl to produce an acid-free organic product which, optionally, may undergo further purification using one or any combination of purification techniques that are known in the art.

The reaction may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

In general, the effluent from the dehydrochlorination reactor may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used, HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

The HFO-1234 so produced is then contacted with the molecular sieves, in accordance with the present invention, to remove the $CF_3C\equiv CH$ impurity. In an embodiment, before the removal of the $CF_3C\equiv CH$ impurity from the HFO-1234, the concentration of the $CF_3C\equiv CH$ impurity present may be measured using techniques known in the art, such as gas chromatography.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

The term "% by GC-FID", as used herein, means the percentage of the peak area measured on the GC-FID spectrum.

Activation of Zeolite

Zeolites were activated following procedures below before use in Examples 1-13.

Zeolite was heated in air at a rate of 30° C./minute to 525° C. and held at 525° C. for 10 minutes. It was then heated to 550° C. at a rate of 2° C./minute and held at 550° C. for 8 hours before cooled to 110° C.

Examples 1-2 (Comparative)

Examples 1-2 demonstrate that the $CF_3C\equiv CH$ impurity contained in HFO-1234yf can not be removed by zeolite 3A. Zeolite 3A has a pore opening of about 3 Angstroms and has a Sanderson electronegativity of about 2.25.

A gaseous HFO-1234yf sample containing $CF_3C\equiv CH$ impurity as indicated in Table 1 passed through a scrubber (7 inch length, 1.25 inch ID) containing about 100 ml activated zeolite 3A at room temperature. The effluent gas from the scrubber was analyzed by GC and GC-MS. The analysis results are also listed in Table 1.

Examples 3-4 (Comparative)

Examples 3-4 demonstrate that the $CF_3C\equiv CH$ impurity contained in HFO-1234yf can not be removed by zeolite 4A. Zeolite 4A has a pore opening of about 4 Angstroms and has a Sanderson electronegativity of about 2.32.

A gaseous HFO-1234yf sample containing $CF_3C\equiv CH$ impurity as indicated in Table 1 passed through a scrubber (7 inch length, 1.25 inch ID) containing about 100 ml activated zeolite 4A at room temperature. The effluent gas from the scrubber was analyzed by GC and GC-MS. The analysis results are also listed in Table 1.

Examples 5-7

Examples 5-7 demonstrate that the concentration of the $CF_3C\equiv CH$ impurity in its mixture with HFO-1234yf can be substantially reduced after contacting with zeolite 5A. Zeolite 5A has a pore opening of about 5 Angstroms and has a Sanderson electronegativity of about 2.56.

A gaseous HFO-1234yf sample containing $CF_3C\equiv CH$ impurity as indicated in Table 1 passed through a scrubber (7 inch length, 1.25 inch ID) containing about 100 ml activated zeolite 5A at room temperature. The effluent gas from the scrubber was analyzed by GC and GC-MS. The analysis results are also listed in Table 1.

Examples 8-9

Examples 8-9 demonstrate that the concentration of the $CF_3C\equiv CH$ impurity in its mixture with HFO-1234yf can be substantially reduced after contacting with zeolite 13X.

Zeolite 13X has a pore opening of about 8 Angstroms and has a Sanderson electronegativity of about 2.38.

A gaseous HFO-1234yf sample containing $CF_3C\equiv CH$ impurity as indicated in Table 1 passed through a scrubber (7 inch length, 1.25 inch ID) containing about 100 ml activated zeolite 13X at room temperature. The effluent gas from the scrubber was analyzed by GC and GC-MS. The analysis results are also listed in Table 1.

Examples 10-11 (Comparative)

Examples 10-11 demonstrate that the $CF_3C\equiv CH$ impurity contained in HFO-1234yf can not be removed by zeolite CBV-600. Zeolite CBV-600 has a pore opening of about 8 Angstroms and has a Sanderson electronegativity of about 2.95.

A gaseous HFO-1234yf sample containing $CF_3C\equiv CH$ impurity as indicated in Table 1 passed through a scrubber (7 inch length, 1.25 inch ID) containing about 100 ml activated zeolite CBV-600 at room temperature. The effluent gas from the scrubber was analyzed by GC and GC-MS. The analysis results are also listed in Table 1.

Example 12

Example 12 demonstrates that the concentration of the $CF_3C\equiv CH$ impurity in its mixture with HFO-1234yf can be reduced after contacting with zeolite AW-300. Zeolite AW-300 has a pore opening of about 4 Angstroms and has a Sanderson electronegativity of about 2.85.

A gaseous HFO-1234yf sample containing $CF_3C\equiv CH$ impurity as indicated in Table 1 passed through a scrubber (7 inch length, 1.25 inch ID) containing about 100 ml activated zeolite AW-300 at room temperature. The effluent gas from the scrubber was analyzed by GC and GC-MS. The analysis results are also listed in Table 1.

Example 13

Example 13 demonstrates that the concentration of the $CF_3C\equiv CH$ impurity in its mixture with HFO-1234yf can be reduced after contacting with zeolite AW-500. Zeolite AW-500 has a pore opening of about 4 Angstroms and has a Sanderson electronegativity of about 2.77.

A gaseous HFO-1234yf sample containing $CF_3C\equiv CH$ impurity as indicated in Table 1 passed through a scrubber (7 inch length, 1.25 inch ID) containing about 100 ml activated zeolite AW-500 at room temperature. The effluent gas from the scrubber was analyzed by GC and GC-MS. The analysis results are also listed in Table 1.

TABLE 1

| Example No. | Scrubber Zeolite | Rate (sccm) | $CF_3C\equiv CH$ Concentration (% by Flow GC-FID) Before Scrubbing | After Scrubbing | Change of $CF_3C\equiv CH$ Concentration |
|---|---|---|---|---|---|
| 1 | 3A | 24.7 | 0.17 | 0.17 | 0% |
| 2 | 3A | 11.1 | 0.17 | 0.17 | 0% |
| 3 | 4A | 25.0 | 0.17 | 01.7 | 0% |
| 4 | 4A | 9.4 | 0.17 | 0.17 | 0% |
| 5 | 5A | 25.0 | 0.21 | 0.12 | −45% |
| 6 | 5A | 24.7 | 0.15 | 0.11 | −31% |
| 7 | 5A | 11.1 | 0.15 | 0.09 | −43% |
| 8 | 13X | 27.0 | 0.19 | 0.15 | −23% |
| 9 | 13X | 11.1 | 0.20 | 0.12 | −39% |
| 10 | CBV-600 | 10.7 | 0.15 | 0.15 | 0% |
| 11 | CBV-600 | 26.8 | 0.163 | 0.165 | 0.02% |
| 12 | AW-300 | 10.3 | 0.134 | 0.117 | −13% |
| 13 | AW-500 | 9.2 | 0.118 | 0.107 | −9% |

Note that not all of the activities described above in the general description or the examples are required, that a portion of a specific activity may not be required, and that one or more further activities may be performed in addition to those described. Still further, the order in which activities are listed is not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising:
   contacting a mixture comprising at least one fluoroolefin and at least one impurity with at least one zeolite to reduce the concentration of said at least one impurity in said mixture;
   wherein said at least one zeolite is selected from the group consisting of zeolite 5A, zeolite 13X, zeolite LSX, zeolite AW-300, and mixtures thereof.

2. The process according to claim 1 wherein the at least one fluoroolefin is a hydrofluoroolefin.

3. The process according to claim 1 wherein the at least one fluoroolefin is a hydrochlorofluoroolefin.

4. The process according to claim 1 wherein the at least one fluoroolefin is $CF_3CF=CH_2$, $CF_3CH=CHF$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, or mixtures thereof.

5. The process according to claim 1 wherein the at least one fluoroolefin is $CF_3CF=CH_2$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, or mixtures thereof.

6. The process according to claim 2 wherein the at least one hydrofluoroolefin is $CF_3CF=CH_2$, $CF_3CH=CHF$, $CF_3CH=CH_2$, $CF_3CH=CF_2$, $CF_3CF=CHF$, or mixtures thereof.

7. The process according to claim 2 wherein the at least one hydrofluoroolefin is $CF_3CF=CH_2$, $CF_3CH=CH_2$, $CF_3CH=CF_2$, $CF_3CF=CHF$, or mixtures thereof.

8. The process according to claim 3 wherein the at least one hydrochlorofluoroolefin is $CF_3CCl=CH_2$, $CF_3CH=CHCl$, $CF_3CF=CHCl$, $CF_3CH=CCl_2$, $CF_3CCl=CHCl$, $CF_3CH=CFCl$, $CF_3CCl=CHF$, or mixtures thereof.

9. The process according to claim 1 wherein the at least one fluoroolefin is $CF_3CF=CH_2$.

10. The process according to claim 1 wherein the at least one fluoroolefin is $CF_3CCl=CH_2$, $CF_3CH=CHCl$, or mixtures thereof.

11. The process according to claim 1 wherein the amount of the at least one fluoroolefin is at least 70 wt % of the mixture.

12. The process according to claim 1 wherein the amount of the at least one fluoroolefin is at least 90 wt % of the mixture.

13. A composition formed by the process of claim 1.

14. A composition comprising:
   i. a mixture of at least one fluoroolefin and at least one impurity; and
   ii. at least one zeolite selected from the group consisting of zeolite 5A, zeolite 13X, zeolite LSX, zeolite AW-300, and mixtures thereof.

15. The composition according to claim 14 wherein the at least one fluoroolefin is a hydrofluoroolefin.

16. The composition according to claim 14 wherein the at least one fluoroolefin is a hydrochlorofluoroolefin.

17. The composition according to claim 14 wherein the at least one fluoroolefin is $CF_3CF=CH_2$, $CF_3CH=CHF$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, or mixtures thereof.

18. The composition according to claim 14 wherein the at least one fluoroolefin is $CF_3CF=CH_2$, $CF_3CH=CH_2$, $CF_3CCl=CH_2$, $CF_3CH=CHCl$, $CF_3CH=CFCl$, $CF_3CH=CF_2$, $CF_3CCl=CHF$, $CF_3CF=CHF$, $CF_3CF=CHCl$, $CF_3CH=CCl_2$, $CF_3CCl=CHCl$, or mixtures thereof.

19. The composition according to claim 15 wherein the at least one hydrofluoroolefin is $CF_3CF=CH_2$, $CF_3CH=CHF$, $CF_3CH=CH_2$, $CF_3CH=CF_2$, $CF_3CF=CHF$, or mixtures thereof.

20. The composition according to claim 15 wherein the at least one hydrofluoroolefin is $CF_3CF=CH_2$, $CF_3CH=CH_2$, $CF_3CH=CF_2$, $CF_3CF=CHF$, or mixtures thereof.

21. The composition according to claim 16 wherein the at least one hydrochlorofluoroolefin is $CF_3CCl=CH_2$, $CF_3CH=CHCl$, $CF_3CF=CHCl$, $CF_3CH=CCl_2$, $CF_3CCl=CHCl$, $CF_3CH=CFCl$, $CF_3CCl=CHF$, or mixtures thereof.

22. The composition according to claim 14 wherein the at least one fluoroolefin is $CF_3CF=CH_2$.

23. The composition according to claim 14 wherein the at least one fluoroolefin is $CF_3CCl=CH_2$, $CF_3CH=CHCl$, or mixtures thereof.

24. The composition according to claim 14 wherein the amount of the at least one fluoroolefin is at least 70 wt % of the mixture.

25. The composition according to claim 14 wherein the amount of the at least one fluoroolefin is at least 90 wt % of the mixture.

26. The composition according to claim 14 wherein the amount of the at least one impurity in the mixture is 300 ppm or less.

27. The composition according to claim 14 wherein the amount of the at least one impurity in the mixture is 200 ppm or less.

28. The composition according to claim 14 wherein the amount of the at least one impurity in the mixture is 100 ppm or less.

29. The composition according to claim 14 wherein the amount of the at least one impurity is at least 0.15% by GC-FID of the mixture.

30. The composition according to claim 14 wherein the amount of the at least one impurity is at least 0.118% by GC-FID of the mixture.

* * * * *